(12) United States Patent
Hendrikse et al.

(10) Patent No.: US 10,578,526 B2
(45) Date of Patent: Mar. 3, 2020

(54) IN SITU CHEMICAL TRANSFORMATION AND IONIZATION OF INORGANIC PERCHLORATES ON SURFACES

(71) Applicant: Smiths Detection Montreal Inc., Mississauga, Ontario (CA)

(72) Inventors: Jan Hendrikse, Whitby (CA); Vladimir Romanov, Vaughan (CA)

(73) Assignee: SMITHS DETECTION MONTREAL INC., Mississauga, Ontario (CA)

( * ) Notice: Subject to any disclaimer, the term of this patent is extended or adjusted under 35 U.S.C. 154(b) by 211 days.

(21) Appl. No.: 14/907,196

(22) PCT Filed: Jul. 24, 2014

(86) PCT No.: PCT/CA2014/050702
§ 371 (c)(1),
(2) Date: Jan. 22, 2016

(87) PCT Pub. No.: WO2015/010212
PCT Pub. Date: Jan. 29, 2015

(65) Prior Publication Data
US 2016/0161379 A1    Jun. 9, 2016

Related U.S. Application Data

(60) Provisional application No. 61/857,721, filed on Jul. 24, 2013.

(51) Int. Cl.
*G01N 1/44* (2006.01)
*H01J 49/16* (2006.01)

(52) U.S. Cl.
CPC ............... *G01N 1/44* (2013.01); *H01J 49/16* (2013.01)

(58) Field of Classification Search
CPC ...... G01N 1/44; G01N 1/02; G01N 2001/028; H01J 49/142; H01J 49/16
See application file for complete search history.

(56) References Cited

U.S. PATENT DOCUMENTS 5,118,937 A    6/1992    Hillenkamp et al.
8,129,677 B2   3/2012    Truche et al.
(Continued)

FOREIGN PATENT DOCUMENTS

EA    15051 B1       4/2011
JP    2001006606 A   1/2001
(Continued)

OTHER PUBLICATIONS

Garcia-Reyes et al, "Detection of Explosives and Related Compounds by Low-Temperature Plasma Ambient Ionization Mass Spectrometry", Anal. Chem., 2011, v. 83, pp. 1084-1092; published on-line Dec. 21, 2010.*
(Continued)

*Primary Examiner* — Robert J Eom
(74) *Attorney, Agent, or Firm* — Kevin E. West; Advent, LLP

(57) ABSTRACT

A method for providing in situ chemical transformation and ionization of a portion (e.g., inorganic oxidizer) of a sample via an analyte detection system is disclosed herein. The method includes introducing a gas into an ionization source of the analyte detection system via an inlet. The method further includes generating ions within the ionization source and directing the gas and generated ions through and out of the ionization source and to the sample. The sample is located proximal to the ionization source in an ambient environment. The ions chemically react with the sample and desorb and ionize an analyte from the sample, the analyte being generated from the inorganic oxidizer, the desorbed analyte having a lower melting point and/or better desorp-
(Continued)

tion kinetics than the inorganic oxidizer. The method further includes receiving the desorbed analyte via an analyzer of the analyte detection system.

12 Claims, 6 Drawing Sheets

(56) References Cited

U.S. PATENT DOCUMENTS

| | | |
|---|---|---|
| 8,410,432 B2 | 4/2013 | Miller et al. |
| 2010/0078550 A1 | 4/2010 | Wiseman et al. |
| 2011/0042560 A1 | 2/2011 | Ouyang et al. |
| 2012/0325024 A1 | 12/2012 | Vidal-de-Miguel et al. |
| 2013/0040402 A1 | 2/2013 | Yang et al. |

FOREIGN PATENT DOCUMENTS

| | | |
|---|---|---|
| RU | 2285253 C1 | 10/2006 |
| RU | 95845 C1 | 7/2010 |
| RU | 2434225 C1 | 11/2011 |
| WO | 2009102766 A1 | 8/2009 |
| WO | 2010039675 A1 | 4/2010 |
| WO | 2011041416 A2 | 4/2011 |

OTHER PUBLICATIONS

Garcia-Reyes, Juan F., et al. "Detection of explosives and related compounds by low-temperature plasma ambient ionization mass spectrometry." Analytical chemistry 83.3 (2010): 1084-1092.*
Mäkinen, Marko, Marjaana Nousiainen, and Mika Sillanpää. "Ion spectrometric detection technologies for ultra-traces of explosives: A review." Mass spectrometry reviews 30.5 (2011): 940-973.*
Pavlov, Julius, and Athula B. Attygalle. "Direct detection of inorganic nitrate salts by ambient pressure helium-plasma ionization mass spectrometry." Analytical chemistry 85.1 (2012): 278-282.*
Cheng, Shasha, et al. "Dopant-assisted negative photoionization ion mobility spectrometry for sensitive detection of explosives." Analytical chemistry 85.1 (2012): 319-326.*
Extended European Search Report dated Jan. 20, 2017 for EP Application No. 14830194.8.
International Search Report dated Oct. 29, 2014 for International Appln. No. PCT/CA2014/050702.
Russian Search Report dated Apr. 13, 2018.
Chinese Search Report dated Feb. 2, 2018.
Juan F. Garcia-Reyes, et al., "Detection of Explosives and Related Compounds by Low-Temperature Plasma Ambient Ionization Mass Spectrometry". Dec. 21, 2010. vol. 83, pp. 1084-1092.
Russian Office Action dated Apr. 13, 2018.
Chinese Office Action dated Feb. 2, 2018.
Office Action for Chinese Application No. 2016-528271, dated May 22, 2018.

* cited by examiner

```
                                                    ┌─ 500
                                                   ╱
┌─────────────────────────────────────────────────────────┐
│  INTRODUCING A TRANSPORT GAS INTO A DIELECTRIC BARRIER OF│
│   AN IONIZATION SOURCE VIA AN INLET PORT OF THE IONIZATION│
│                      SOURCE 502                          │
└─────────────────────────────────────────────────────────┘
                            ↓
┌─────────────────────────────────────────────────────────┐
│   APPLYING A VOLTAGE OR CURRENT BETWEEN A FIRST AND      │
│  SECOND ELECTRODE OF THE IONIZATION SOURCE TO GENERATE   │
│  AN ELECTRIC FIELD, THE ELECTRIC FIELD GENERATING IONS THE│
│   FIRST ELECTRODE AND SECOND ELECTRODE BEING SEPARATED   │
│              BY THE DIELECTRIC BARRIER 504               │
└─────────────────────────────────────────────────────────┘
                            ↓
┌─────────────────────────────────────────────────────────┐
│    DIRECTING THE TRANSPORT GAS AND GENERATED IONS        │
│            THROUGH THE ELECTRIC FIELD 506                │
└─────────────────────────────────────────────────────────┘
                            ↓
┌─────────────────────────────────────────────────────────┐
│  DIRECTING THE IONS OUT OF THE IONIZATION SOURCE AND TO A│
│   SAMPLE FOR DESORBING AN ANALYTE FROM THE SAMPLE, THE   │
│    SAMPLE BEING IN AN AMBIENT ENVIRONMENT, THE SAMPLE    │
│   INCLUDING AN INORGANIC OXIDIZER, WHEREIN THE IONS ARE  │
│  SUITABLE FOR GENERATING THE ANALYTE FROM THE INORGANIC  │
│    OXIDIZER, THE ANALYTE BEING MORE VOLATILE THAN THE    │
│                 INORGANIC OXIDIZER 508                   │
└─────────────────────────────────────────────────────────┘
                            ↓
┌─────────────────────────────────────────────────────────┐
│   RECEIVING THE DESORBED ANALYTE VIA AN ANALYZER 510     │
│  ┌───────────────────────────────────────────────────┐   │
│  │   RECEIVING THE DESORBED ANALYTE VIA A CAPILLARY  │   │
│  │                  INTERFACE 512                    │   │
│  └───────────────────────────────────────────────────┘   │
│                          ↓                               │
│  ┌───────────────────────────────────────────────────┐   │
│  │   DIRECTING THE DESORBED ANALYTE THROUGH THE      │   │
│  │     CAPILLARY INTERFACE TO THE ANALYZER 514       │   │
│  └───────────────────────────────────────────────────┘   │
└─────────────────────────────────────────────────────────┘
```

IN SITU CHEMICAL TRANSFORMATION AND IONIZATION OF INORGANIC PERCHLORATES ON SURFACES

REFERENCE TO RELATED APPLICATION

This application claims priority to U.S. Provisional Patent Application Ser. No. 61/857,721 entitled "In Situ Chemical Transformation and Ionization of Inorganic Perchlorates on Surfaces" filed Jul. 24, 2013, which is incorporated by reference.

BACKGROUND

Desorption-based detection systems are commonly implemented for identifying chemical agents in samples. Currently available desorption-based detection systems, such as swab desorption-based ion mobility spectrometry systems, are very good at detecting a substance when the substance can evaporate upon heating to a reasonable temperature (e.g., below 250 degrees Celsius). Alternatively, the currently available desorption-based detection systems are also very good at detecting a substance if the substance decomposes upon heating into characteristic substance(s) that can readily evaporate and be detected. However, some samples include substances (e.g., analytes, chemical agents), which are desirable to detect, but do not possess the above-referenced characteristics.

SUMMARY

A method for providing in situ chemical transformation and ionization of an inorganic oxidizer of a sample via an analyte detection system is disclosed herein. The method includes introducing a gas into an ionization source of the analyte detection system via an inlet port of the ionization source. The method further includes directing the gas through the ionization source to generate ions. The method further includes directing the ions out of the ionization source and to the sample, the sample being located proximal to the ionization source, the sample also being located in an ambient environment. The ions chemically react with the sample and desorb an analyte from the sample, the analyte being generated from the inorganic oxidizer, the desorbed analyte having a lower melting point and/or better desorption kinetics than the inorganic oxidizer. The method further includes receiving the desorbed analyte via an analyzer of the analyte detection system.

An analyte detection system for performing a method for providing in situ chemical transformation and ionization of an inorganic oxidizer of a sample is disclosed herein. The system includes an ionization source. The ionization source is configured for generating ions within the ionization source using an electric discharge, directing the ions out of the ionization source and to a sample located proximal to the ionization source using a gas flow, the sample being located in an ambient environment, wherein the ions chemically react with the sample to desorb an analyte from the sample. The system further includes an analyzer, such as a mass spectrometer, an ion mobility spectrometer, or a combination of the two, configured for receiving and analyzing the desorbed analyte from the sample. Further, the sample includes an inorganic oxidizer, such as a chlorate or perchlorate. The desorbed analyte is generated from the chemical reaction between the ions and the inorganic oxidizer. The desorbed analyte has a lower melting point or better desorption kinetics than the inorganic oxidizer.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

BRIEF DESCRIPTION OF THE DRAWINGS

The detailed description is described with reference to the accompanying figures. In the figures, the left-most digit(s) of a reference number identify the figure in which the reference number first appears. The use of the same reference number in different instances in the description and the figures may indicate similar or identical items.

FIG. 5 is a flow diagram illustrating a method for providing in situ chemical transformation and ionization of an inorganic oxidizer of a sample via an analyte detection system using, for example, the analyte detection system illustrated in FIG. 1, in accordance with example implementations of the present disclosure.

DETAILED DESCRIPTION

Figure 1:
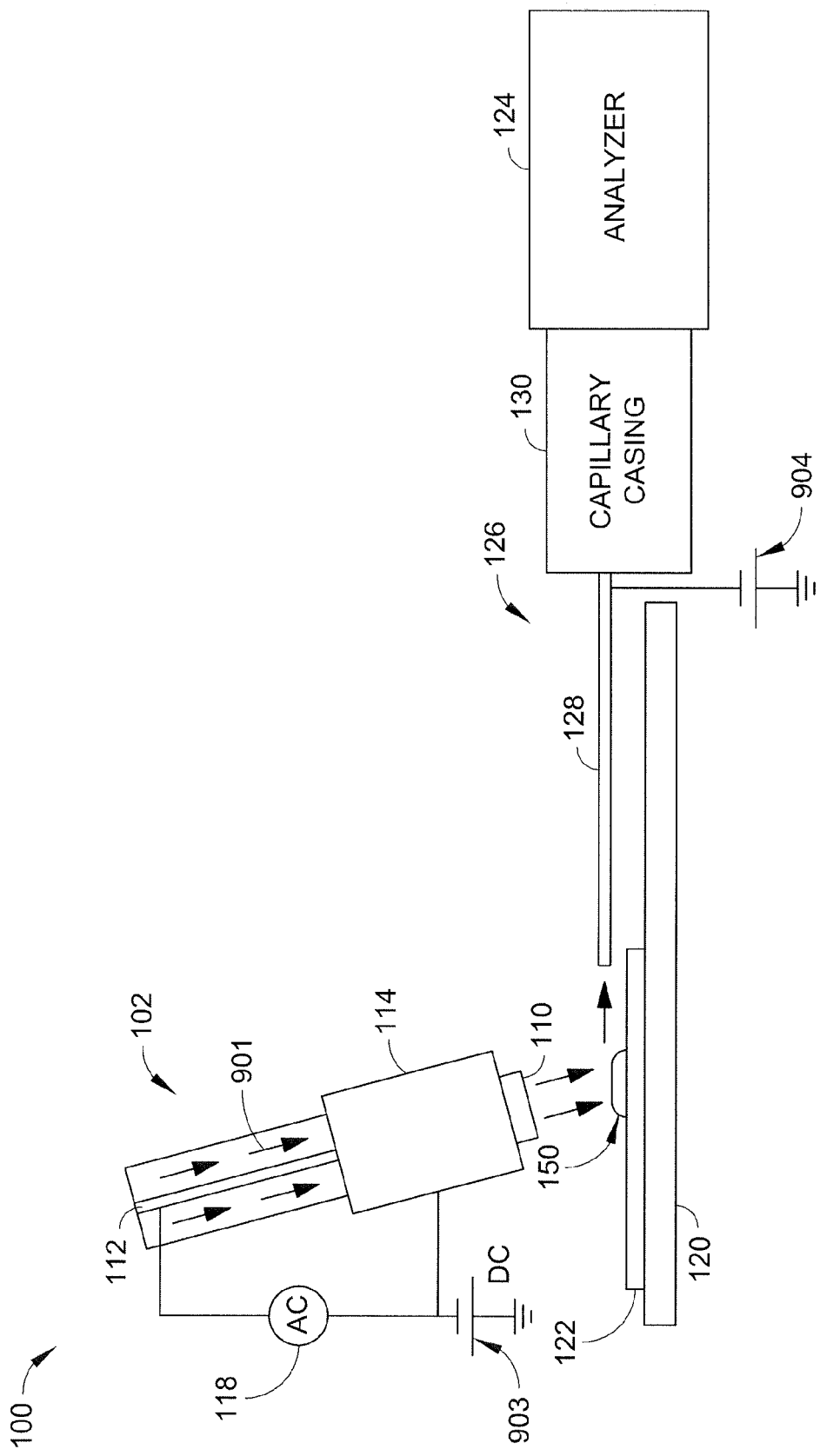
FIG. 1 is a conceptual schematic block diagram illustration of an analyte detection system including a partial view of an ionization source of the system in accordance with an example implementation of the present disclosure.

FIG. 1 is an illustration of an analyte detection system (e.g., sample analysis system, chemical agent detector) 100. The analyte detection system 100 includes an ionization source (e.g., a surface ionization source) 102. In embodiments, the ionization source 102 is configured for desorbing and ionizing at least one analyte included in a sample material (e.g., sample) 150. In embodiments, the ionization source 102 is a dielectric barrier discharge ion source. For example, the ionization source 102 is a low temperature plasma (LTP) probe.

Figure 2A:
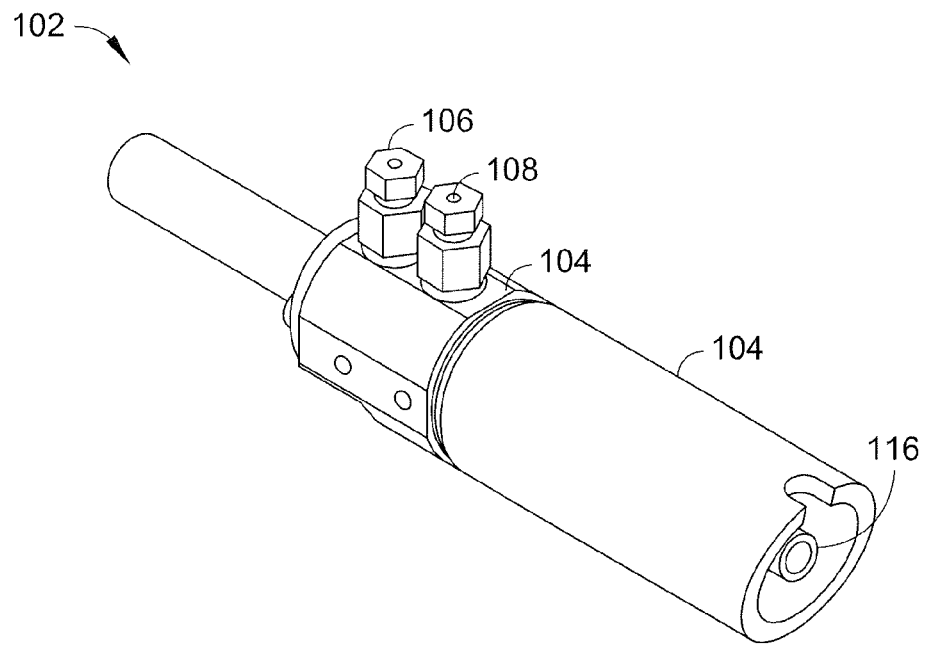
FIG. 2A is a partial view of an ionization source of an analyte detection system in accordance with an example implementation of the present disclosure.
Figure 2B:
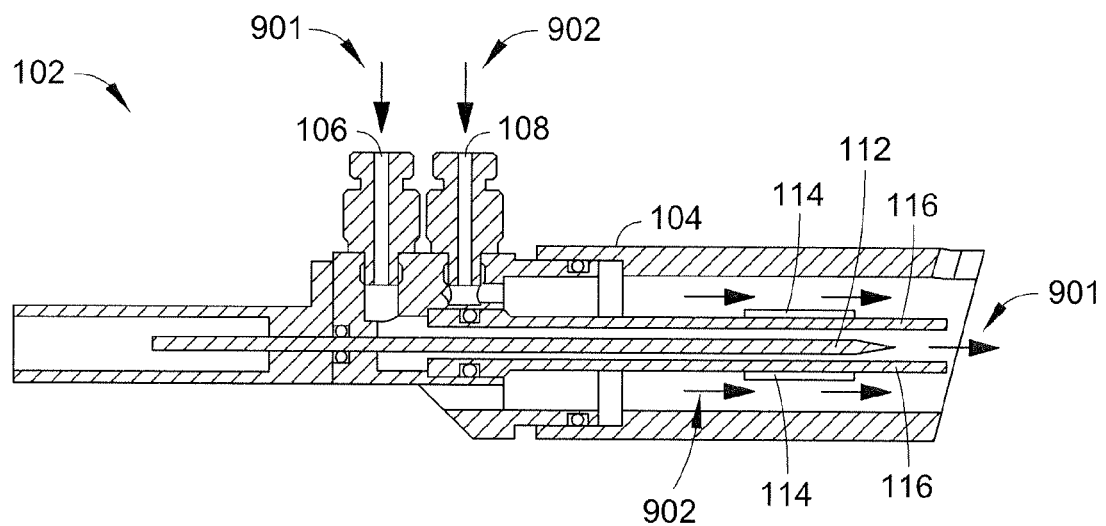
FIG. 2B is a partial cross-sectional view of the ionization source shown in FIG. 2A in accordance with example implementations of the present disclosure.

Referring generally to FIGS. 1, 2A and 2B (FIGS. 1, 2A and 2B), in embodiments, the ionization source (e.g., LTP probe) 102, includes a housing 104, the housing including one or more inlet ports (106, 108). In exemplary embodiments, port 106 is a transport gas inlet port and port 108 is a dopant gas inlet port. In embodiments, the ionization source (e.g., LTP probe) 102 includes a probe tip 110. In embodiments, the ionization source (e.g., LTP probe) 102 includes a first electrode 112. For example, the first electrode 112 is a needle electrode. In embodiments, the first electrode 112 is composed of an electrically conducting material, such as stainless steel.

In embodiments, the ionization source (e.g., LTP probe) 102 includes a second electrode 114. For example, the second electrode 114 is a counter electrode, a sleeve electrode, and/or an outer electrode 114. In embodiments, the second electrode 114 is composed of an electrically conducting material, such as copper tape.

In embodiments, the ionization source (e.g., LTP probe) 102 includes a dielectric barrier 116. In embodiments, the dielectric barrier 116 is formed of an electrically insulating material. For example, the electrically insulating material is glass, quartz, ceramics and polymers. In embodiments, the dielectric barrier 116 is configured for electrically separating the first electrode 112 from the second electrode 114. For example, the dielectric barrier 116 is a glass tube that is open at both ends. In embodiments, the first electrode 112 extends into the housing 104 and into a proximal end of the dielectric barrier (e.g., glass tube) 116. In embodiments, the second electrode 114 may or may not be in contact with an exterior portion of the dielectric barrier (e.g., glass tube) 116. In some embodiments, the first electrode 112 is axially centered within the dielectric barrier (e.g., glass tube) 116.

In embodiments, the ionization source (e.g., LTP probe) 102 includes or is configured for being connected to an alternating current (AC) power supply 118. The power supply 118 is configured for applying a voltage or current to the first electrode 112 or the second electrode 114 to generate a low temperature plasma by creating an electric field in the gas. For example, the applied current is an alternating current (AC) or a direct current (DC). In some embodiments, the first electrode 112 is grounded and the second electrode 114 receives voltage from the power supply 118. In other embodiments, the second electrode 114 is grounded and the first electrode 112 receives voltage from the power supply 118. In other embodiments, both electrodes (112, 114) are connected to a first DC power supply 903 that lifts the voltage to a level similar to the voltage applied to the instrument inlet by a second DC power supply 904. In embodiments, the second DC power supply 904 may be necessary to operate the analyzer 124 properly, or it may just happen to be the way a legacy analyzer has been designed.

In embodiments, a transport gas flow is supplied to the ionization source (e.g., LTP probe) 102 via the one or more inlet ports (e.g., transport gas and/or dopant gas inlet ports) (106 or 108) of the ionization source 102 and flows through the ionization source 102. For example, the transport gas may be any type of gas, such as helium, nitrogen gas, argon, compressed air, ambient air, dry air, etc. In embodiments, the low temperature plasma is propelled through and out of the ionization source (e.g., LTP probe) 102 by the transport gas flow (e.g., continuous gas flow). A specific dopant molecule may be added to the gas flow in port 106 so that, in the discharge region, ions are formed that are beneficial to the reaction with the sample and formation of the analyte. A dopant molecule may be added to the gas flow through port 108 so that it can react with the ions created in the discharge region, or with the sample without being subjected to the discharge itself.

In embodiments, the plasma is a low temperature plasma (LTP). The LTP can be characterized as a non-equilibrium plasma having high energy electrons, with relatively low kinetic energy but reactive ions and neutrals. In embodiments, the LTP is an ambient plasma which can be used to desorb and ionize analytes from surfaces and produce molecular ions or fragment ions of the analytes. In embodiments, the analyte ions may be lactate nitrate ions, lactate-nitrate ions, lactate ions and/or nitrate ions. In embodiments, the plasma is a non-thermal, low power plasma which is created between the electrodes (112, 114), with the dielectric limiting the displacement current. The plasma contains reactive ions, electrons, radicals, excited neutrals and metastable species in the ambient environment of the sample 150 which can be used to desorb/ionize molecules in situ from a solid sample (e.g., sample 150 which is in the solid phase), as well as ionizing liquids and gases (e.g., sample 150 which is in the liquid phase or gas phase). The plasma can be extracted from the discharge region (e.g., dielectric barrier 116) and directed towards the sample (e.g., sample surface) 150 by the gas flow, assisted diffusion and/or the electric field generated by any space charge generated if the plasma is unbalanced. For instance, the plasma is propelled out of a distal end (e.g., probe tip 110) of the dielectric barrier (e.g., glass tube) 116. In embodiments, the plasma contacts the sample 150 at substantially atmospheric pressure. In some embodiments, the plasma contacts the sample 150 in an ambient environment.

In embodiments, varying the electric field adjusts the energy and fragmentation degree of ions generated from the analytes in a sample 150.

In an exemplary experimental setup, the system 100 can include a sample platform 120 upon which a sample slide 122 can be placed. In embodiments, the sample 150 is deposited upon the slide 122. The sample platform 120, sample slide 122 and sample 150 can be positioned proximal to the outlet of the distal (e.g., bottom) end of the dielectric barrier (e.g., glass tube) 116 for allowing the plasma exiting the ionization source (e.g., LTP probe) 102 to contact the sample 150. In embodiments, the system 100 can include heating elements (e.g., not shown) for heating the sample 150 to further promote desorption and ionization of analyte(s) from the sample 150 by the plasma.

In embodiments, the system 100 includes an analyzer (e.g., detector) 124. In embodiments, the analyzer 124 may or may not be coupled with the ionization source 102. In embodiments, the analyzer 124 is located in sufficient proximity to the sample 150 to collect and analyze ions of at least one analyte of the sample 150 produced by the ionization source 102. In some embodiments, the analyzer 124 is a mass spectrometer (e.g., mass spectrometry system). In other embodiments, the analyzer 124 is an ion mobility spectrometer (ion mobility spectrometry system).

In embodiments, such as shown in FIG. 1, the system 100 includes an interface 126 to the analyzer 124. In embodiments, the interface 126 is directly connected to an inlet of the detector (e.g., the analyzer) 124. In embodiments, the inlet of the analyzer 124 is configured for continuous transfer of desorbed analyte from the sample 150 to the analyzer 124. In embodiments, the interface 126 is proximal to the ionization source 102 and the sample 150 and is configured for receiving and directing desorbed and ionized analytes from the sample 150 to the analyzer 124. In embodiments, such as shown in FIG. 1, interface 126 is a capillary interface. For example, the capillary interface 126 includes a capillary 128 connected to a capillary casing 130. Further, capillary interface 126 can be configured for heating the ionized analytes received from the sample 150 (e.g., is a heated capillary interface).

In embodiments in which the ionization source 102 is an LTP probe as discussed above, the LTP probe 102 shown in FIG. 1 provides a mechanism for separating the ionization source 102 from an inlet of the detector (e.g., analyzer) 124.

As mentioned above, the ionization source 102 can desorb and ionize analytes from surfaces and produce molecular ions and/or fragment ions of the analytes for mass analysis. In embodiments, the ratio between the different ions produced can be adjusted by varying the electric field, the transport gas type, and/or the transport gas flow rate. In some embodiments, the ratio between the different ions produced can be adjusted by adjusting the overlap of the electrodes (112, 114) that are used to establish the electric field.

In embodiments, a reagent can be added to the transport gas flow 901 via inlet port 106 for reactively desorbing the analyte from a surface. For example, the reagent generates reagent ions that reactively desorb the analyte from a surface. In further embodiments, reagent is added to the gas flow 902 through port 108 to mix with the ion transport flow 901 in the vicinity of the sample 150 to generate primary ions that reactively desorb the analyte from the surface. In further embodiments, reagent is added that interacts as neutrals with the ions and the sample analytes. In further embodiments, the neutrals that are also created by the ion source 102 are transported by the gas flow 901 to the sample, react there to form a neutral analyte, which is re-ionized before entering the analyzer 124. This allows analysis by analyzers 124 that have an inlet that is at a high potential without the need of a DC offset. In embodiments, neutral species may be added to the transport gas flow 901 to enhance formation of analytes.

In embodiments, the sample 150 is of biological origin. In further embodiments, the sample 150 is an industrial work piece or pharmaceutical product or ingredient. In further embodiments, the sample 150 is a food or food ingredient, a toxin, a drug, an explosive, a bacterium, or a biological tissue.

In embodiments, the sample 150 includes inorganic oxidizers, such as chlorates. For example, the sample 150 can include chlorates such as sodium chlorate ($NaClO_3$). The term "chlorate(s)" as described herein encompasses chemical compounds containing the chlorate anion ($ClO_3$) and salts of chloric acid. In further embodiments, the sample 150 includes inorganic oxidizers, such as perchlorates. For example, the sample 150 can include perchlorates such as sodium perchlorate ($NaClO_4$), potassium perchlorate ($KClO_4$), and/or ammonium perchlorate ($NH_4ClO_4$). The term "perchlorate(s)" as described herein encompasses salts derived from perchloric acid ($HClO_4$). Typically, chlorates and perchlorates have very high melting points and/or tend to decompose rather than evaporate when heated which can make them difficult to detect via an analyzer 124. In embodiments, the plasma can include nitrate ions ($NO_3$), $HNO_3$ ($NO_3$)$^-$ ions, nitrate cluster ions, and/or nitric acid ($HNO_3$) vapor, which are used to concurrently generate and ionize a compound from the sample 150 which is more volatile than the inorganic oxidizer(s) of the sample 150, and thus, more easily detectable via a analyzer (e.g., mass spectrometer, ion mobility spectrometer) 124. For example, if the sample 150 includes a perchlorate, the perchlorate chemically reacts with ions (e.g., nitrate ions) of the plasma to form another substance (e.g., a substance having a lower melting point than the perchlorate, such as a nitrate-chlorate compound (e.g., nitryl perchlorate) or a nitrate-chlorate ion (e.g., ($HNO_3$)$ClO_3^-$), and it is this lower melting point substance (e.g., vapor including the nitrate-chlorate compound/ion) that is collected and analyzed (e.g., detected) by the system 100. Thus, the perchlorate is converted through its reaction with the nitrate ions, into a much more volatile chemical (e.g., nitrate-chlorate compound/ion) that can evaporate off of the surface of the sample 150 and can be more easily collected and analyzed/detected by the analyzer 124. In some embodiments, the nitrate-chlorate compound/ion is forced to lose the nitric acid group ($HNO_3$) through collisions with neutral gas atoms, leaving the chlorate ion ($ClO3^-$) to be detected and analyzed. In embodiments, the nitrate-chlorate compound evaporates off of the surface of the sample 150 via a combination of heat, transport gas flow, and electric field. In embodiments, sufficient energy is supplied to allow the ionization source (e.g., LTP probe) 102 to create ions (e.g., nitrate ions) at room temperature and atmospheric pressure. Further, the transport gas flow brings the ions (e.g., nitrate ions) to the sample 150 (e.g., perchlorate-containing sample).

In embodiments, the sample 150 is a nitrate ($NO_3$)-containing sample. In embodiments, in order to detect the nitrate, ions are generated by the ionization source 102 via an electric discharge. For example, ammonia ($NH_3$), a lactate salt, lactic acid or urea is introduced into the ionization source (e.g., LTP probe) 102 via gas flow 901, for example, by leading the flow through a solid-state cartridge (not shown) before entering port 106. Further, the ammonia is then led over the discharge in order to ionize the ammonia. The low temperature plasma which exits the LTP probe 102 includes the ionized ammonia which reacts with the sample (e.g., nitrate sample) 150 to form ammonium nitrate ($NH_4NO_3$). The ammonium nitrate then evaporates from the surface (e.g., from the sample 150) and is collected and analyzed by the analyzer (e.g., ion mobility spectrometer and/or mass spectrometer) 124. In another example, lactate ions are added to gas flow 902 through port 108, and are allowed to mix with gas flow 901 just before interacting with the sample, but bypassing the plasma.

In other embodiments, the ionization source 102 can be one of a number of different types, including but not limited to: a Corona discharge ionization source, a glow discharge ionization source, an ionization source which implements alpha radiation from Americium-241 (Am241), and an electrospray ionization source. In embodiments, all of the above-mentioned ionization source types can produce nitrate ions. In other embodiments, the ion source is a microplasma discharge, or any other kind of discharge that can be used to generate ions from a gas. In embodiments, the ionization source 102 may use, but is not limited to using, one or more of the following to create ions: a Corona discharge, a dielectric barrier discharge, a low temperature plasma, atmospheric pressure chemical ionization, a flowing atmospheric pressure afterglow, and/or a microhollow cathode discharge.

Figure 4:
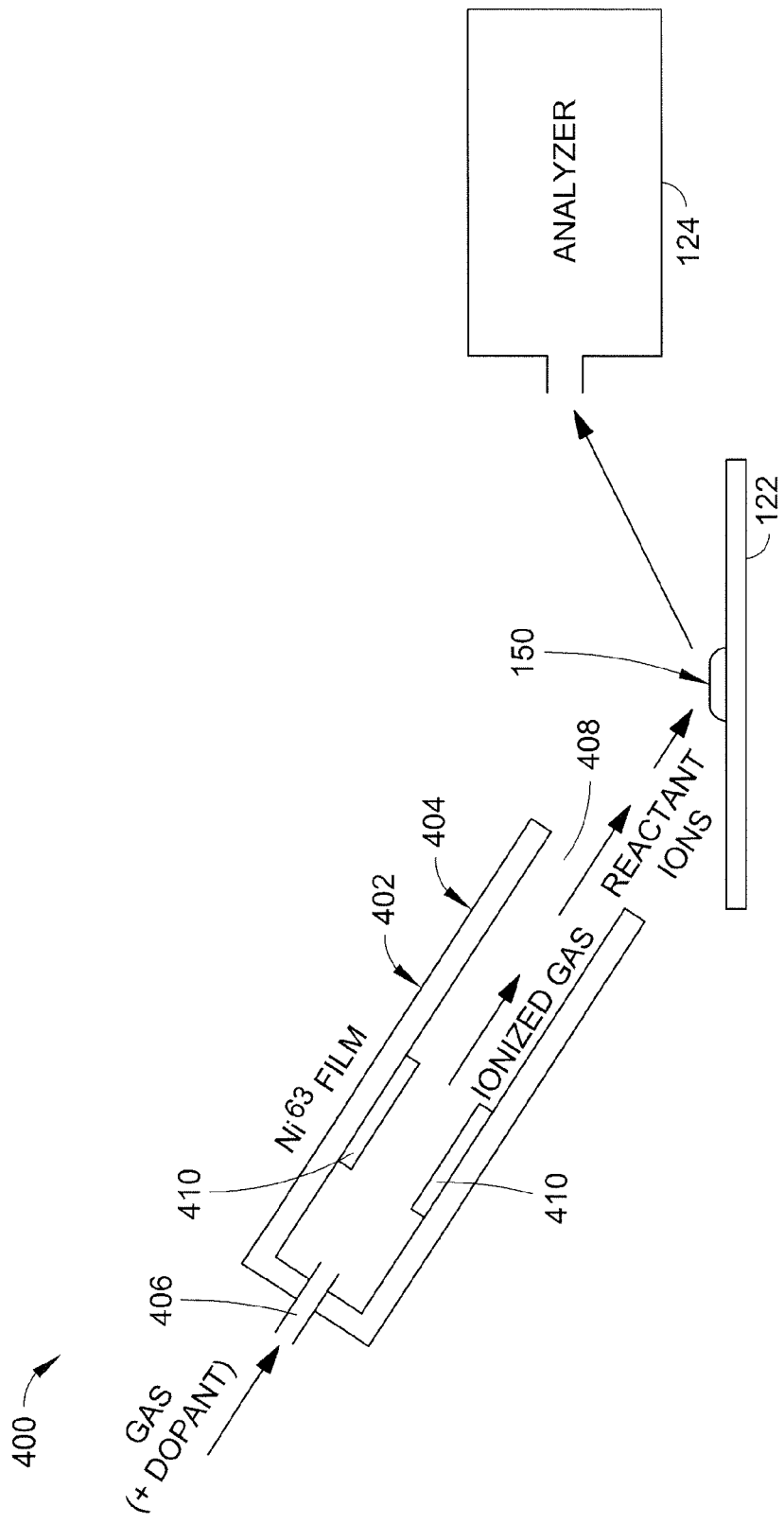
FIG. 4 is a conceptual block diagram illustration of an analyte detection system in accordance with a still further example implementation of the present disclosure.

Referring to FIG. 4 (FIG. 4), an analyte detection system 400 in accordance with a further exemplary embodiment of the present disclosure is shown. In embodiments, the analyte detection system 400 includes an ionization source 402, the ionization source 402 being a Nickel-63 ($Ni^{63}$)-based ionization source. In embodiments, the $Ni^{63}$-based ionization source 402 includes a tube (e.g., a metal tube) 404 having an inlet 406 and an outlet 408 (e.g., two open ends). In embodiments, gas (e.g., carrier gas) is introduced into the inlet (e.g., a heated gas inlet) 406 of the tube 404. For example, the gas is bottled nitrogen dioxide ($NO_2$). In embodiments, a dopant can also be introduced into the inlet 406 of the tube 404. For example, the dopant is ammonium nitrate ($NH_4NO_3$) dopant. In embodiments, the ionization source 402 includes a $Ni^{63}$ film 410 which is located on an interior surface of the tube 404. In embodiments, as the gas (or gas+dopant) is/are directed through the tube 404 over the $Ni^{63}$ film 410 and towards the outlet 408, the gas becomes ionized (e.g., reactant ions are generated from the gas). In other embodiments, nitrate neutrals are provided by the tube 404. In embodiments, the generated ions or nitrate neutrals are directed out of the tube 404, via the outlet 408, and towards the sample 150. In embodiments, the generated ions or nitrate neutrals react with the sample 150 to cause one or more analytes to be desorbed and ionized. The desorbed and ionized analyte(s) are then collected and analyzed by analyzer (e.g., detector, mass spectrometer, ion mobility spectrometer) 124. When using the $Ni^{63}$-based ionization source 402, no interface (e.g., capillary interface) 126 to the analyzer 124 is needed, such that the desorbed/ionized analytes of the sample can evaporate directly into an inlet of the analyzer (e.g., mass spectrometer) 124.

In embodiments, radio frequency (RF) power between the electrodes (112, 114) can be varied/changed/adjusted for causing the ionization source 102 to generate different ion chemistries (e.g., ions other than nitrates) for allowing different analytes of the sample 150 to be detected in a similar way. Thus, the ionization source 102 can switch between ion chemistries by switching the RF power. In further embodiments, volatile compounds (e.g., volatile chemicals) can be mixed with the source gas (e.g., transport gas) to create a similar effect (e.g., to switch between ion chemistries). For example, the volatile chemicals can be mixed into the source gas 901 and led over an AC discharge to create compounds that are advantageous by adding them through port 106. In other embodiments, if the AC discharge would otherwise break them down, the volatile chemicals could be mixed into the source gas after (e.g., downstream from) the AC discharge by introducing them via port 108. In still further embodiments, the volatile chemicals could be applied (e.g., introduced, mixed into the source gas flows 901 and/or 902) intermittently using an on-demand vapor generator (not shown).

Figure 3:
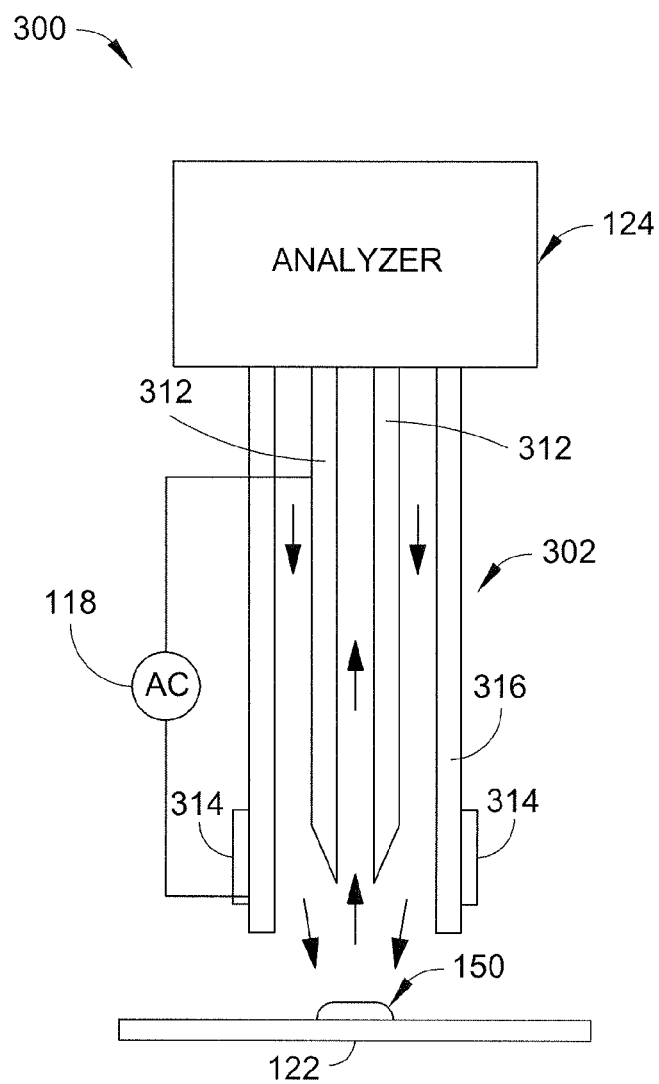
FIG. 3 is a conceptual block diagram illustration of an analyte detection system in accordance with a further example implementation of the present disclosure.

In embodiments, the nitrate-generating discharge described above can be produced using alternative geometries. FIG. 3 (FIG. 3) illustrates an exemplary alternative analyte detection system 300 including an alternative geometry for an ionization source. In embodiments, the ionization source (e.g., low temperature plasma probe) 302 shown in FIG. 3 is generally configured and functions in a generally similar manner to the ionization source 102 discussed above. In embodiments, counter electrode 314 is located on an outer surface of dielectric barrier (e.g., glass tube having two open ends) 316. Further, a central electrode 312 is located inside of the dielectric barrier (e.g., glass tube) 316 in concentric orientation relative to the dielectric barrier (e.g., glass tube) 316. The central electrode 312 of the ionization source 302 shown in FIG. 3 differs from the needle electrode 112 of the ionization source 102 shown in FIG. 1, in that the central electrode 312 is configured for allowing continuous passage of gas, vapor, chemicals, ions, etc. (e.g., analytes) of the sample 150 into and through the central electrode 312 (e.g., the central electrode 312 is hollow). Further, the ionization source 302 shown in FIG. 3 further differs from the ionization source 102 shown in FIG. 1 in that the ionization source 302 of FIG. 3 is configured for being directly connected to an inlet of the analyzer (e.g., detector, mass spectrometer, ion mobility spectrometer) 124. Further, in exemplary embodiments, the ionization source 302 shown in FIG. 3 forms a concentric ring around the inlet of the analyzer 124. In further exemplary embodiments, the central electrode 312 of the ionization source 302 may be directly connected to the inlet of the analyzer 124. In other embodiments, the central electrode may be the inlet of the analyzer 124. Further, the ionization source 302 allows for re-circulated flow of gas, vapor, etc. through the ionization source 302, as shown in FIG. 3. In embodiments, the $Ni^{63}$-based ionization source 402 (shown in FIG. 4), may be implemented in combination with ionization source 302 (shown in FIG. 3).

In other embodiments, compounds or intermediates other than nitrate-chlorate compound can be produced via interaction between the sample 150 and ions provided via the ionization source 102. For example, compounds or intermediates that can be produced via interaction between the sample 150 and ions provided via the ionization source 102 include: nitryl perchlorate ($NO_2ClO_4$), nitrosyl perchlorate ($NOClO_4$), nitryl chlorate ions, nitryl ions, nitryl-chlorate neutrals, nitryl-perchlorate neutrals, and chlorate ions. In embodiments, one or more of the above-referenced compounds or intermediates are subsequently ionized to form ions derived from the above-referenced compounds or intermediates, said ions suitable for being detected by the analyzer 124. For example, nitrate-chlorate ions, nitryl chlorate ions, nitryl perchlorate ions, nitrosyl perchlorate ions, perchlorate ions, and/or chlorate ions may be formed which can be detected by the analyzer 124. In other embodiments, nitryl perchlorate ions and/or nitrosyl perchlorate ions can break down into chlorine gas ($Cl_2$) and chlorine dioxide ($ClO_2$). In embodiments, with nitryl chlorate ions, the nitryl group can be stripped (e.g., removed) to form chlorate ions. In embodiments, nitryl-chlorate neutrals and nitryl-perchlorate neutrals result when nitrate neutrals provided/generated by the ionization source react with chlorate and perchlorate respectively, which are present in the sample. In embodiments, the nitrate neutrals may be directed from the ionization source to the sample 150 (e.g., chlorate sample, perchlorate sample) via flow only. In embodiments, the nitryl-chlorate neutrals and/or nitryl-perchlorate neutrals evaporate from the sample surface via heat and flow. In embodiments, the nitryl-chlorate neutrals and/or nitryl-perchlorate neutrals are ionized.

In further embodiments, multiple nitrate-generating discharges (e.g., ionization sources) can be placed in parallel, if advantageous, to cover a large surface area. In other embodiments, the ionization source can be implemented in a work flow where a surface is first sampled via a swab, then the swab is analyzed. For example, a dielectric barrier discharge ionization source 102 can be used to generate nitrate ions, and the nitrate ions can be directed out of the ionization source 102 using a gas flow (e.g., continuous gas flow) and to the sample 150 disposed on the swab. The nitrate ions can interact with the sample 150 and cause desorption and ionization of one or more analytes from the swab, the desorbed and ionized analytes being provided to an analyzer 124 for analysis.

The analyte detection (e.g., sample analysis) system implementations described herein can be implemented as stand-alone system, or can be incorporated within a larger system, such as a portable chemical detection device. For example, the portable chemical detection device may be configured with a computer system including: a processor; memory; a display; a user interface; hardware; software modules; and firmware.

Example Procedures

The following discussion describes procedures that may be implemented using the above-described implementations of the analyte detection systems (e.g., sample analysis systems) 100, 300 and 400. The procedures are shown as a set of blocks that specify operations performed by one or more devices and are not necessarily limited to the order shown for performing the operations by the respective blocks. In portions of the following discussion, reference will be made to the sample analysis system implementations of FIGS. 1, 3 and 4.

FIG. 5 depicts a procedure (e.g., method, process) 500 in an example implementation for providing in situ chemical transformation and ionization of a portion of a sample (e.g., inorganic oxidizers) on surfaces via the analyte detection system(s) 100, 300 shown in FIGS. 1 and 3. In implementations, the procedure 500 may be performed under automated (e.g., computer) control.

In implementations, the procedure 500 can include introducing a transport gas into a dielectric barrier of an ionization source via an inlet port of the ionization source (block 502). For example, the transport gas may be any type of gas, such as helium, nitrogen gas, argon, compressed air, ambient air, dry air, etc. Further, the ionization source is a dielectric barrier discharge ion source, such as a low temperature plasma probe 102. Further, the dielectric barrier 116 is a glass tube that is open at both ends.

In embodiments, the procedure 500 further includes applying a voltage or current between a first electrode and a second electrode of the ionization source to generate an electric field, the electric field generating ions, the first electrode and second electrode being separated by the dielectric barrier (block 504). For example, the voltage/current is applied via a power supply 118 connected to the LTP probe 102. The voltage/current is applied between the first electrode (e.g., needle electrode) 112 of the LTP probe 102, the first electrode 112 being located within the glass tube 116, and a second electrode (e.g., sleeve electrode) 114 of the LTP probe 102, the second electrode 114 being located on an exterior surface of the glass tube 116.

In embodiments, the procedure 500 further includes directing the transport gas and the generated ions through the electric field (block 506). For example, the generated ions can be nitrate ions. In embodiments, the procedure 500 further includes directing the ions out of the ionization source and to a sample for desorbing an analyte from the sample (block 508), the sample being in an ambient environment, the sample including an inorganic oxidizer, wherein the ions are suitable for generating the analyte from the inorganic oxidizer, the analyte being more volatile than the inorganic oxidizer. For example, the inorganic oxidizer can be a chlorate or perchlorate, while the analyte can be a nitrate-chlorate compound.

In embodiments, the procedure 500 further includes receiving the desorbed analyte via an analyzer (block 510). For example, the desorbed analyte can be received via a mass spectrometer or an ion mobility spectrometer, or a combination of both, which can analyze the analyte to provide information about the sample. In some embodiments, the step of receiving the desorbed analyte via the analyzer includes sub-steps of receiving the desorbed analyte via a capillary interface (block 512) and directing the desorbed analyte through the capillary interface to the analyzer (block 514). For example, the capillary interface 126 is a heated capillary interface connected to the analyzer 124 (e.g., mass spectrometer).

Figure 6:
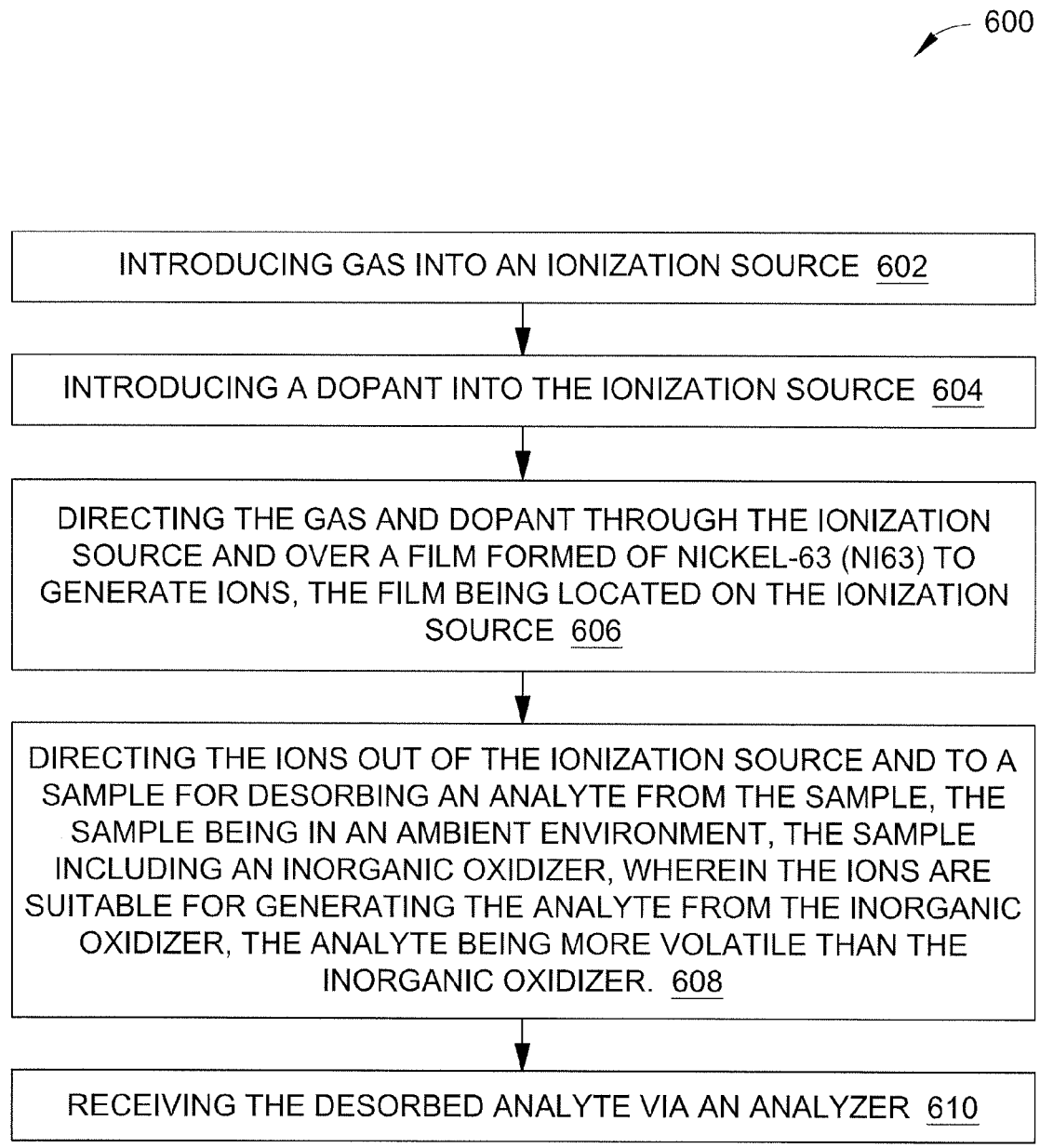
FIG. 6 is a flow diagram illustrating a method for providing in situ chemical transformation and ionization of an inorganic oxidizer of a sample via an analyte detection system using, for example, the analyte detection system illustrated in FIG. 4, in accordance with example implementations of the present disclosure.

FIG. 6 depicts a procedure (e.g., method, process) 600 in an example implementation for providing in situ chemical transformation and ionization of a portion of a sample (e.g., inorganic perchlorates) on surfaces via the analyte detection system 400 shown in FIG. 4. In implementations, the procedure 600 may be performed under automated (e.g., computer) control.

In implementations, the procedure 600 can include introducing gas into an ionization source (block 602). For example, the gas (e.g., nitrogen dioxide) is introduced into the metal tube 404 of the ionization source 402, the metal tube 404 having two open ends (406, 408). In embodiments, the procedure 600 further includes the step of introducing a dopant into the ionization source (block 604). For example, the dopant (e.g., ammonium nitrate) is introduced into the metal tube of the ionization source 402.

In embodiments, the procedure 600 further includes directing the gas and dopant through the ionization source and over a film formed of Nickel-63 ($Ni^{63}$) to generate ions or nitrate neutrals, the film being located on the ionization source. (block 606).

In embodiments, the procedure 600 further includes directing the ions or nitrate neutrals out of the ionization source and to a sample for desorbing and ionizing an analyte from the sample (block 608), the sample being in an ambient environment, the sample including an inorganic oxidizer, wherein the ions or nitrate neutrals are suitable for generating the analyte from the inorganic oxidizer, the analyte being more volatile than the inorganic oxidizer.

In embodiments, the procedure 600 further includes receiving the desorbed analyte via an analyzer (block 610). For example, the desorbed analyte can be received via an inlet of a mass spectrometer or an ion mobility spectrometer, which can analyze the analyte to provide information about the sample.

The methods 500, 600 described herein promote increased detection sensitivity over previously implemented detection methods.

Although the subject matter has been described in language specific to structural features and/or methodological acts, it is to be understood that the subject matter defined in the appended claims is not necessarily limited to the specific features or acts described. Although various configurations are discussed the apparatus, systems, subsystems, components and so forth can be constructed in a variety of ways without departing from this disclosure. Rather, the specific features and acts are disclosed as example forms of implementing the claims.

What is claimed is:

1. A method for providing in situ chemical transformation and ionization of a portion of a sample via an analyte detection system, the method comprising:
  introducing a gas into an ionization source of an analyte detection system via an inlet of the ionization source;
  generating nitrate ions or nitrate cluster ions within the ionization source;
  directing the gas and generated ions through the ionization source; and
  directing the generated ions out of the ionization source and to a sample, the sample being located proximal to the ionization source, the sample located in an ambient environment,
  wherein the generated ions chemically react with the sample and desorb an analyte from the sample, the analyte being generated from a portion of the sample, the portion of the sample being less volatile than the analyte, the portion of the sample being an inorganic oxidizer, the inorganic oxidizer being a chlorate or a perchlorate.

2. The method as recited in claim 1, further comprising:
  receiving the desorbed analyte via an analyzer of the analyte detection system, the analyzer being an ion mobility spectrometer, a mass spectrometer or a combination thereof.

3. The method as recited in claim 2, wherein the step of receiving the desorbed analyte via the analyzer includes:
  receiving the desorbed analyte via a capillary interface of the analyte detection system; and directing the desorbed analyte through the capillary interface to the analyzer.

4. The method as recited in claim 1, wherein the step of generating the ions includes:
applying a voltage between a first electrode and second electrode of the ionization source to generate an electric field which generates the ions; and
varying the electrical field to adjust an energy and fragmentation degree of the generated ions.

5. The method as recited in claim 4, wherein the first electrode and the second electrode are separated by a dielectric barrier.

6. The method as recited in claim 1, wherein the analyte has a lower melting point than the portion of the sample.

7. The method as recited in claim 1, wherein the gas is circulated and re-circulated through the ionization source.

8. The method as recited in claim 1, wherein the analyte is a nitrate-chlorate ion, a nitryl perchlorate ion, or a nitrosyl perchlorate ion.

9. The method as recited in claim 1, wherein the desorbed analyte undergoes chemical reactions to form chlorate ions or perchlorate ions.

10. The method of claim 1, wherein the gas introduced into the ionization source comprises air.

11. The method of claim 10, wherein the gas introduced into the ionization source comprises dry air.

12. A method for providing in situ chemical transformation and ionization of a portion of a sample via an analyte detection system, the method comprising:
introducing a gas into an ionization source of an analyte detection system via an inlet of the ionization source, wherein at least one of the following conditions exists: the ionization source comprises $Ni^{63}$, or the gas being introduced includes a dopant;
generating ions within the ionization source;
directing the gas and generated ions through the ionization source; and
directing the generated ions out of the ionization source and to a sample, the sample being located proximal to the ionization source, the sample located in an ambient environment,
wherein the generated ions chemically react with the sample and desorb an analyte from the sample, the analyte being generated from a portion of the sample, the portion of the sample being less volatile than the analyte, the portion of the sample being an inorganic oxidizer.

* * * * *